United States Patent [19]

Van Vliet

[11] 4,297,157
[45] Oct. 27, 1981

[54] METHOD FOR APPLICATION OF ELASTIC TO ARTICLES

[75] Inventor: Raymond A. Van Vliet, Auburn, Wash.

[73] Assignee: Weyerhaeuser Company, Tacoma, Wash.

[21] Appl. No.: 161,722

[22] Filed: Jun. 23, 1980

[51] Int. Cl.³ .............................................. B32B 31/08
[52] U.S. Cl. .................................. 156/164; 112/262.3; 156/229; 156/265; 156/302; 156/495; 156/520; 156/552
[58] Field of Search ............... 156/163, 164, 229, 269, 156/270, 297, 299, 302, 494, 475, 489, 519, 520, 552, 265, 495; 2/243 R; 112/262.3

[56] References Cited

U.S. PATENT DOCUMENTS

| | | | |
|---|---|---|---|
| 2,289,336 | 7/1942 | Bamford | 156/519 |
| 2,905,581 | 9/1959 | Maxey | 156/163 |
| 3,049,166 | 8/1962 | Clark | 156/489 |
| 3,488,778 | 1/1970 | Goujon et al. | 2/402 |
| 3,560,292 | 2/1971 | Butter | 2/402 |
| 3,663,962 | 5/1972 | Burger | 2/224 A |
| 3,694,815 | 10/1972 | Burger | 2/224 A |
| 3,728,191 | 4/1973 | Wierzba et al. | 156/552 |
| 3,828,367 | 8/1974 | Bourgeois | 2/224 A |
| 3,860,003 | 1/1975 | Buell | 128/287 |
| 3,963,557 | 6/1976 | Patterson | 156/519 |
| 4,081,301 | 3/1978 | Buell | 156/664 |
| 4,239,578 | 12/1980 | Gore | 156/361 |

*Primary Examiner*—Jerome W. Massie
*Attorney, Agent, or Firm*—Weyerhaeuser Company

[57] ABSTRACT

The invention is an improved applicator for placing elastic strips on articles such as garments. A continuous of tensioned elastic is gripped sequentially by two clamping means. The elastic unit thus created is severed from the main body of elastic material. One or both clamping means may be movable to adjust the length of the elastic unit and control the position where it is applied to the article. Preferably the elastic is adhesively bonded but it may also be stitched to the article. As soon as bonding is achieved, the clamps are opened in sequence and return to a starting position to repeat the cycle.

The examples disclose a six-module elastic applicator designed to apply elastic to discrete areas adjacent to the leg openings of disposable diapers. This applicator enables more precise placement of the elastic and virtually eliminates waste.

17 Claims, 16 Drawing Figures

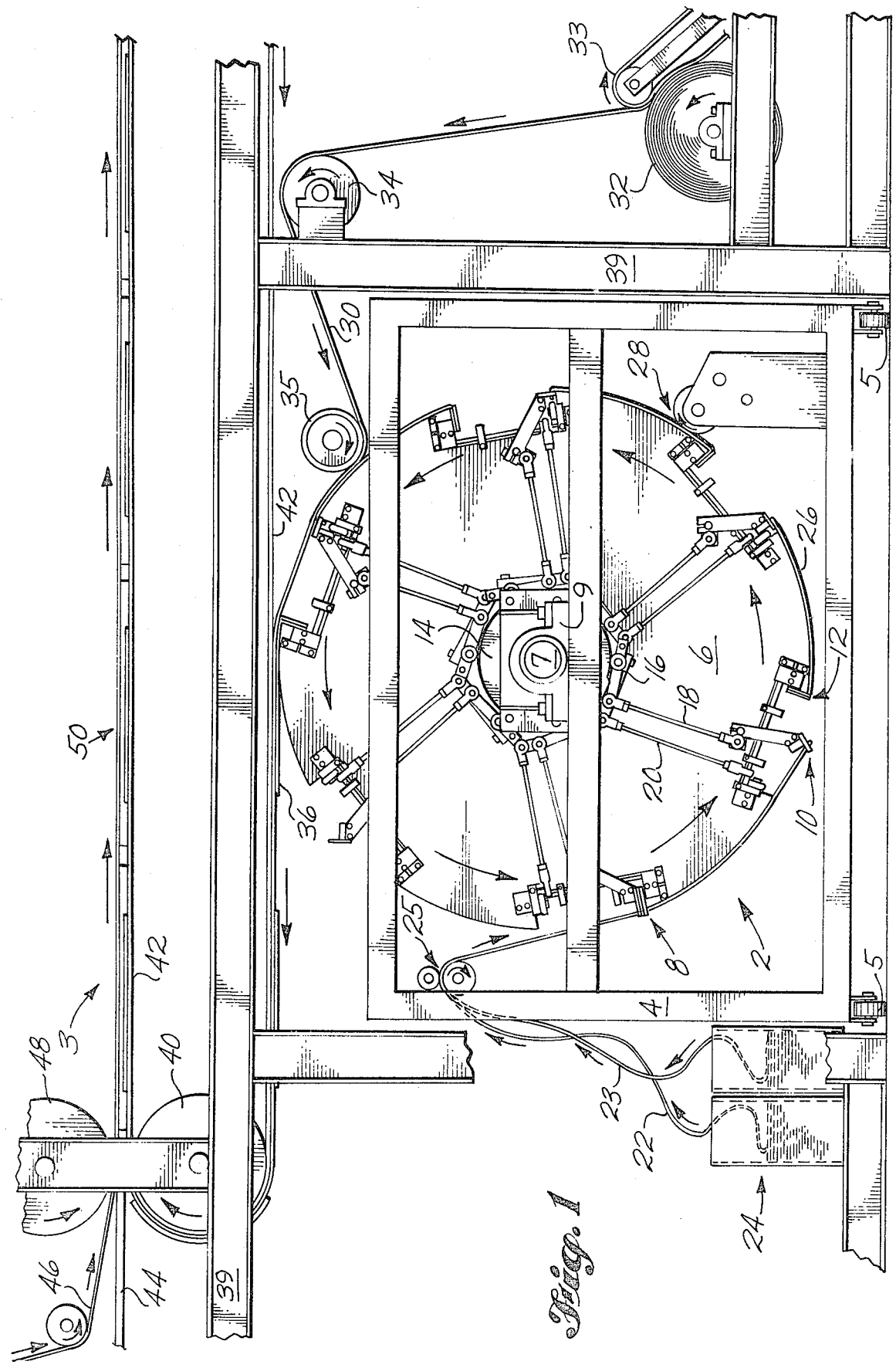

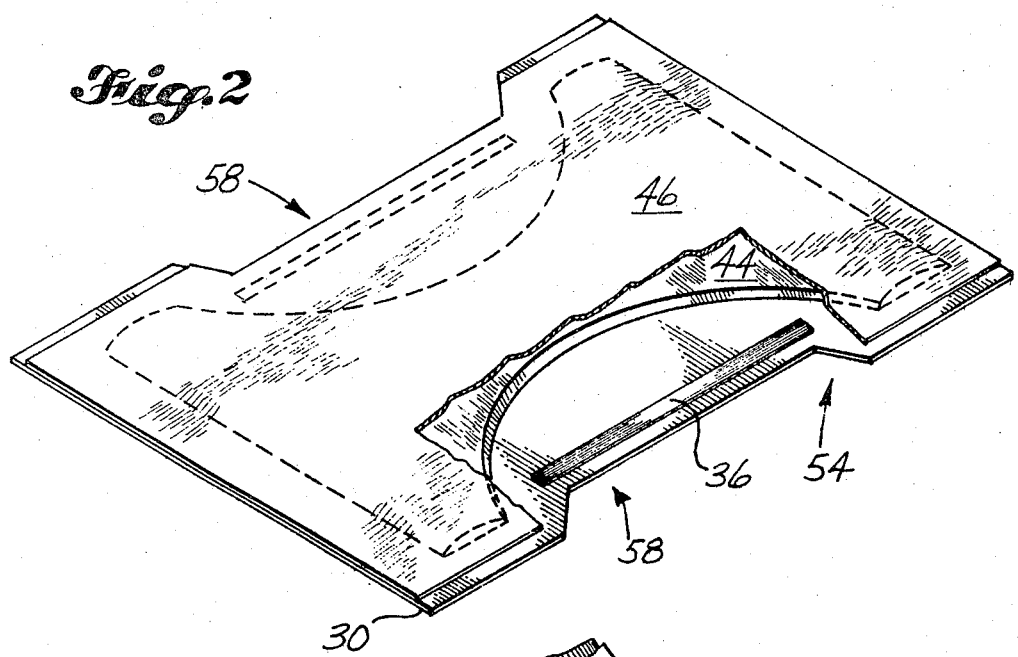
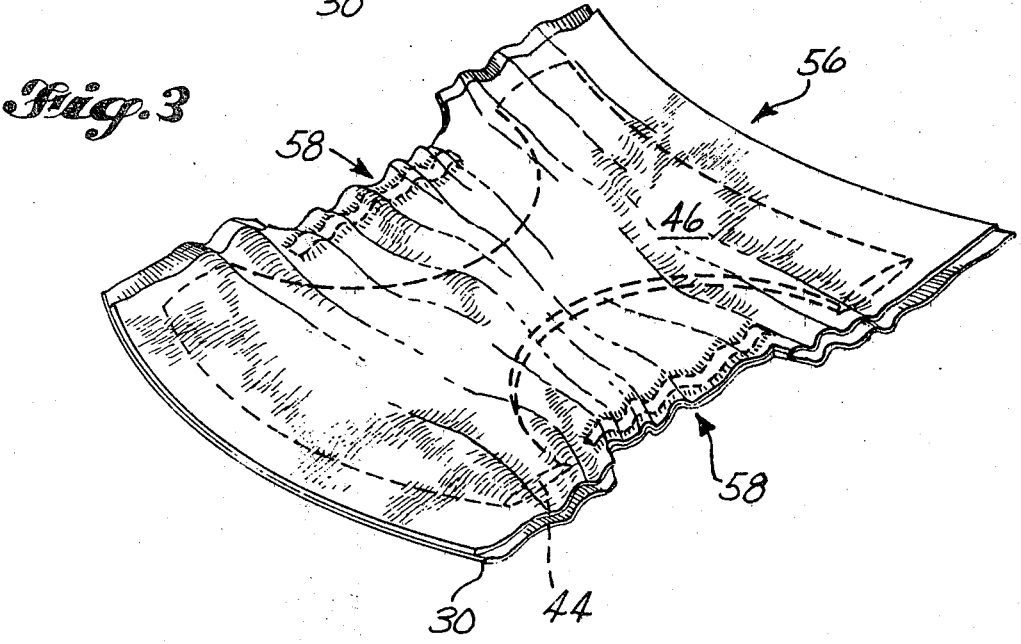

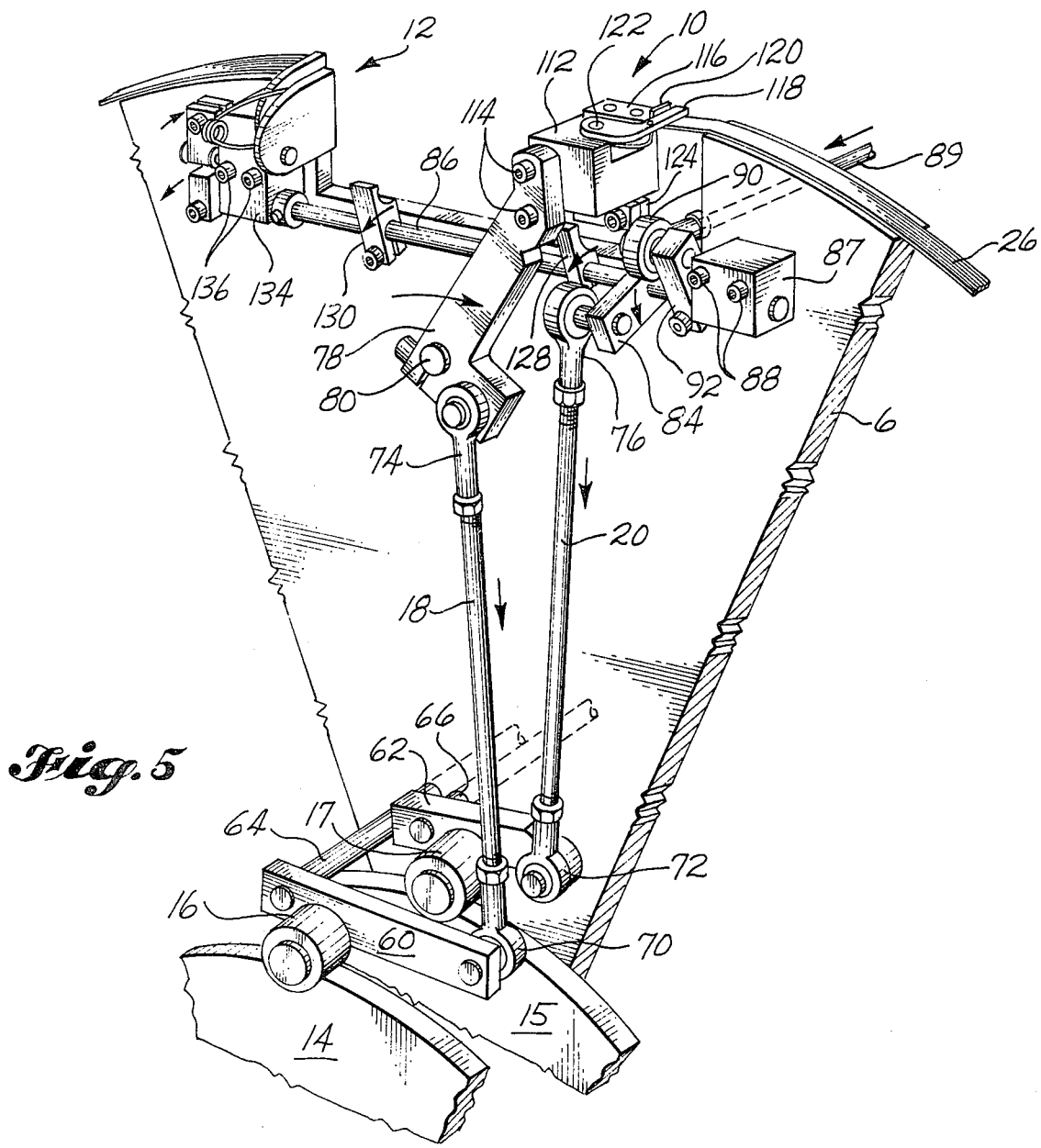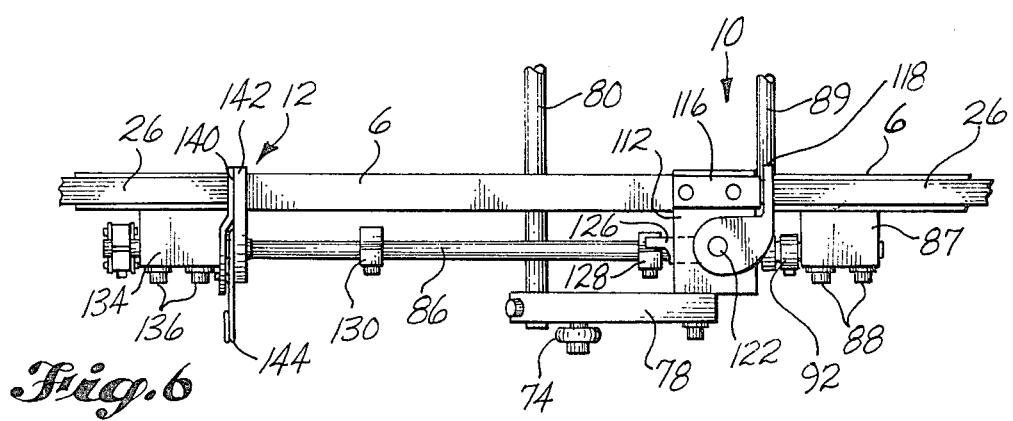

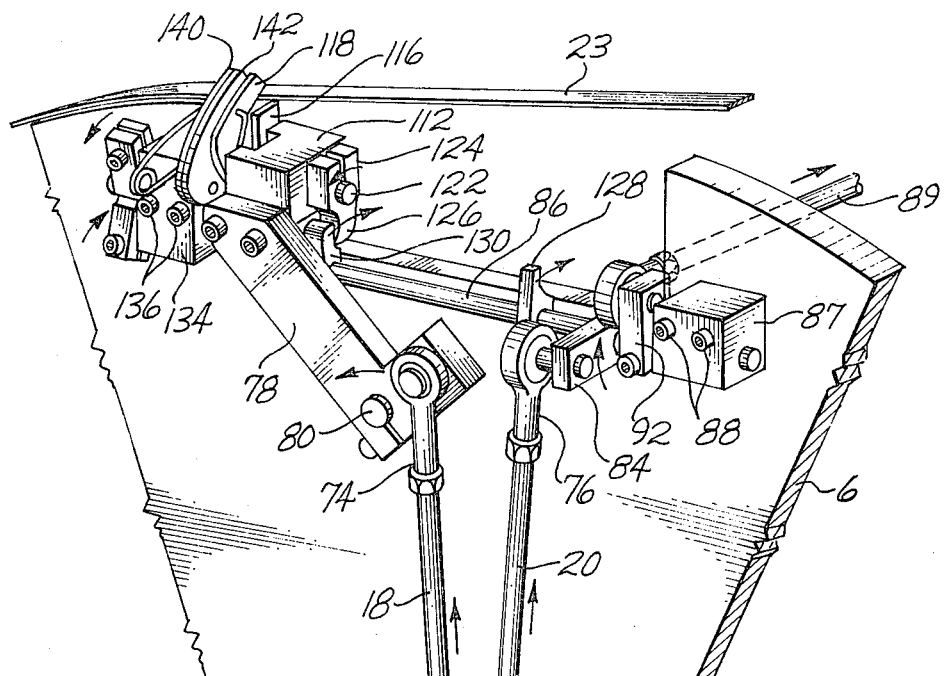
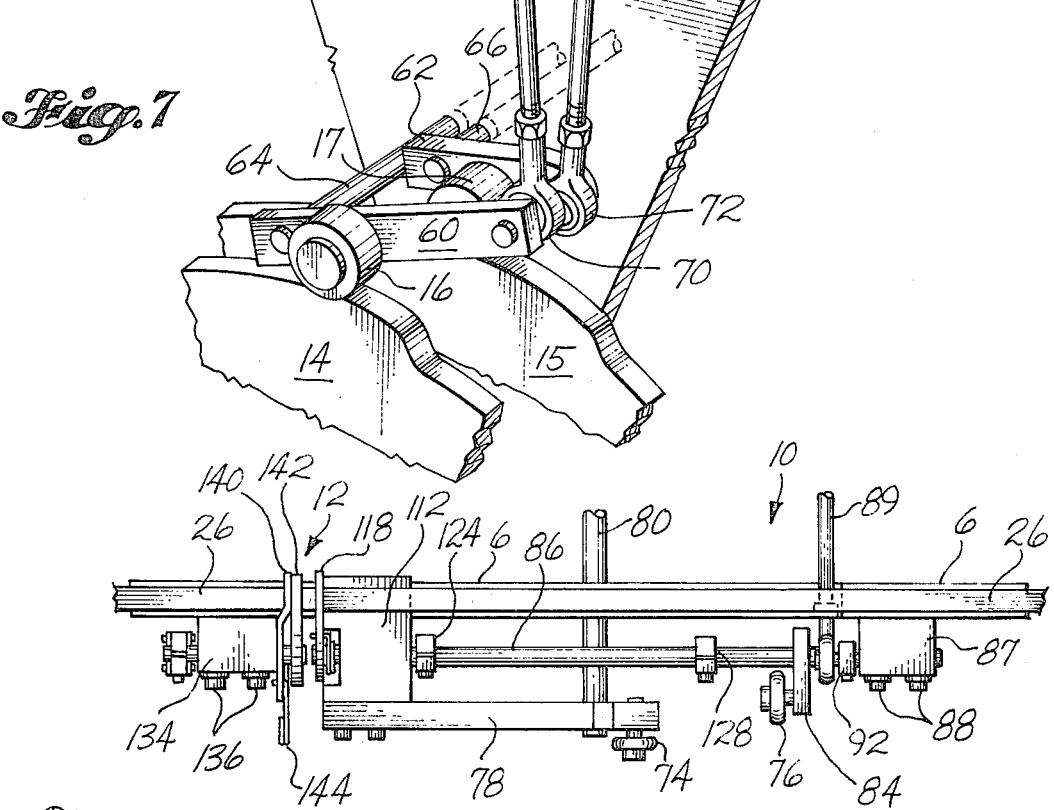

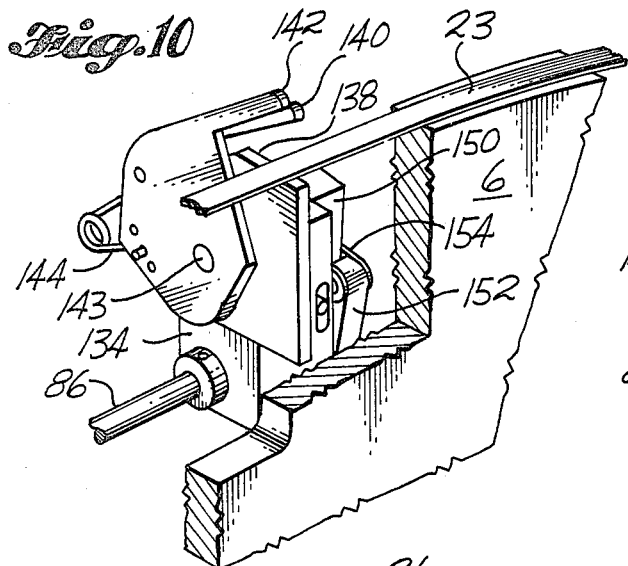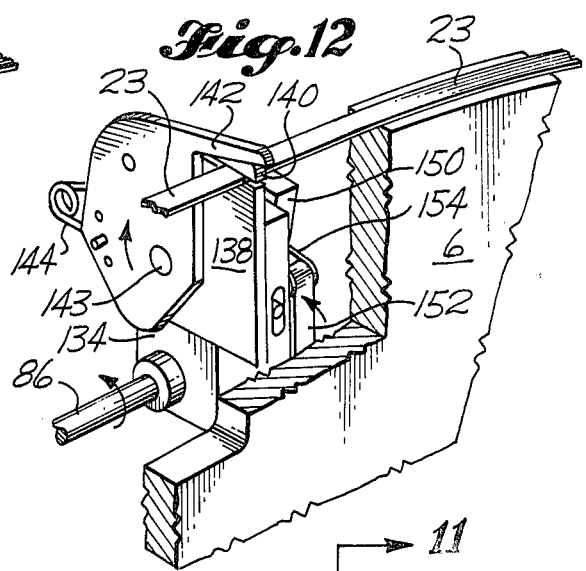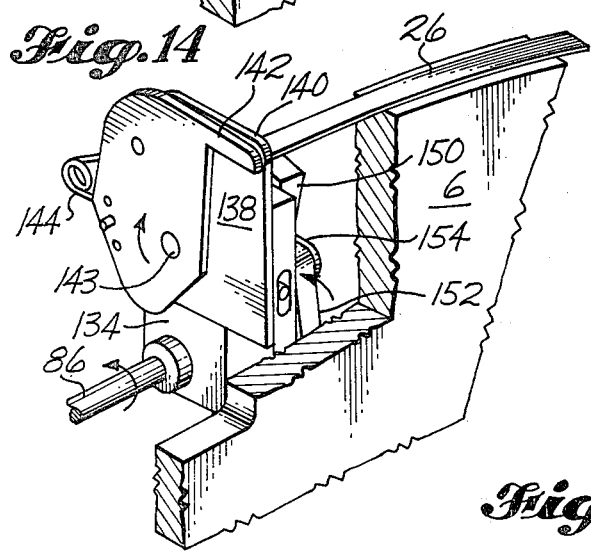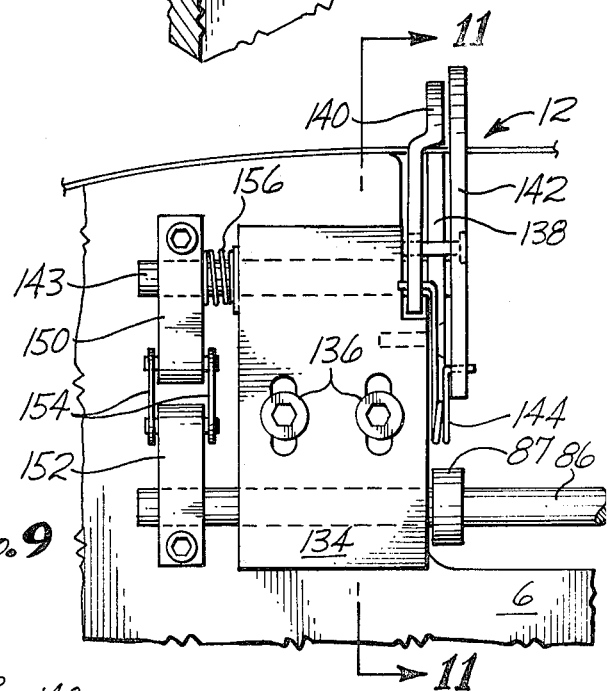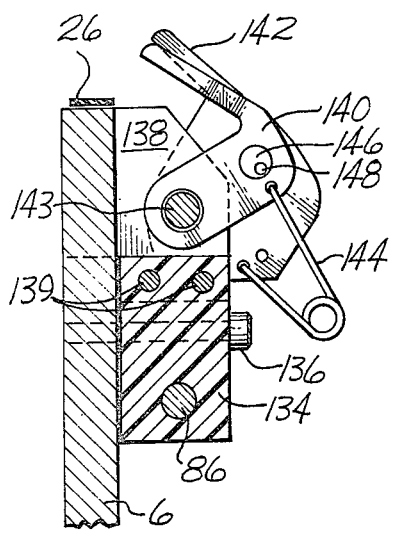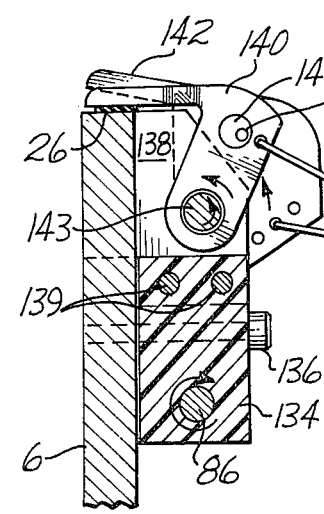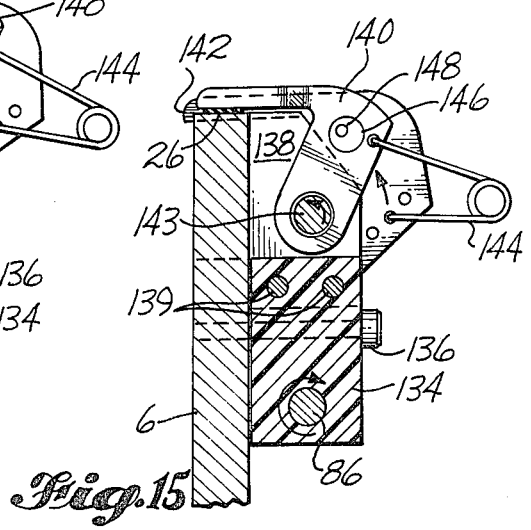

METHOD FOR APPLICATION OF ELASTIC TO ARTICLES

FIELD OF THE INVENTION

This invention is an improved method and apparatus for application of an elastic material to articles of manufacture. In a preferred application it may be used for attaching elastic strips to localized areas of clothing such as disposable undergarments or diapers.

BACKGROUND OF THE INVENTION

Methods for applying elastic to clothing and similar articles are well known in the art. The elastic is normally in the form of a ribbon or tape and is used to provide snug fits around areas such as waist or leg openings. For many years this elastic was attached by hand sewing. With the advent of disposable one-time-use garments the labor cost of hand sewing became prohibitive and other means of application had to be sought. Several patents can be cited as exemplary of the development of the art up to the time of the present invention.

Goujon et al., U.S. Pat. No. 3,488,778, show a disposable panty in which the elastic is apparently applied by glue bonding, although no specific means of accomplishing this is shown.

Butter, U.S. Pat. No. 3,560,292, shows a similar garment in which the elastic is "spot-welded" to the base textile. Again, he does not disclose an apparatus for accomplishing this result at high speed.

Burger, in U.S. Pat. No. 3,663,962, teaches a method of continuously applying longitudinal strips of stretched elastic to a panty-type garment by sewing or adhesive bonding. He deals with the problem of keeping the elastic flat on the material by essentially freeing it in its stretched state during application. This process is further described in U.S. Pat. No. 3,694,815 to the same inventor.

Bourgeois, U.S. Pat. No. 3,828,367, uses an adhesive bonding system to place stretched elastic along the waistline and leg openings of disposable panties. The elastic is applied continuously and severed when each article is trimmed from the continuous sheet of nonwoven material. While this achieves the desired result at the waistline, it leaves a strip of tensioned elastic across the front and rear transverse margins of the crotch or gusset sections. These are areas where elastic is not desirable either from functional or wearer comfort standpoints.

Buell, U.S. Pat. No. 4,081,301, shows in detail a commercially practical system of applying elastic to the leg openings of disposable diapers. Buell has faced two vexiing problems. He has avoided the complexity of applying the elastic in a curvilinear fashion and has substituted a design which allows straight line application. He has also found one solution to the problems of selectively placing the elastic where it is functionally desirable without also having it in places where it is unwanted, such as in Bourgeois.

A diaper made by the Buell process is shown in his patent U.S. Pat. No. 3,860,003. Here the elastic is functional only around the lower two-thirds of the leg opening. This, of course, is the region where leakage is most likely to occur.

One common feature noted in all of these patents is that it is easier to apply the elastic in an uninterrupted linear manner. By uninterrupted is meant in a continuous strand for the full length of the individual article. As seen in Bourgeois this often puts elastic where it is not wanted. Buell deals with this by adhesively bonding the elastic only in the area in which it is functionally desired, even though the tensioned elastic applied is equivalent to the full article length. The elastic strands are severed when the individual diapers are cut from the continuous assembly. This causes each end to relax to the unstretched length. These ends remain present but they serve no useful purpose. However, they tend to be somewhat unsightly from the user standpoint and waste about 20 percent of the relatively expensive elastic ribbon.

It is thus clear the art has not developed fully satisfactory methods for applying tensioned elastic at high speed to specified areas of articles, where such areas are less than the full length or width of the article.

SUMMARY OF THE INVENTION

The present invention is a method and apparatus for applying elastic units to discrete areas of articles when such areas may be of shorter linear dimension than the length of the article itself, as measured along the axis of the elastic. The invention also represents an advance in the art in that essentially all of the elastic is functional when applied to an area of such shorter linear dimension.

The above results are accomplished by a method in which a strip of tensioned elastic material from a supply source is sequentially grasped between two clamping means, then severed from the main source of elastic adjacent to the second clamping means. The elastic unit thus created is held by the clamps until it is applied to the article, or some component of the article, whereupon it is released by the clamps. The bond between the elastic and the article may be achieved by stitching, spot welding, or by the use of an adhesive. In the latter case this can be applied continuously or intermittently to either the elastic unit or the the appropriate area of the article or component to which the elastic unit will later be applied.

In its preferred form the elastic units are bonded by a continuous layer of adhesive applied to all of the elastic except the short terminal portions held in the clamps. Normally, at least 90 percent of the elastic, measured in its untensioned state, will be functionally bonded to the article. More typically, elastic will be about 95% utilized.

The method is particularly well suited for the production of elastic leg disposable diapers. It is usually most convenient to apply the tensioned elastic units to the plastic backing film prior to assembly of the diapers. The film can itself be held in tension through the assembly process to prevent puckering by the elastic. The method is especially well adapted to apply the elastic units to the leg opening area of the diapers with a minimum of waste. The appearance is also improved since there are essentially no loose ends on the elastic strips.

A preferred version of the method uses a plurality of elastic applicator modules that sequentially apply the elastic units to the articles in a repeating cycle. This can most conveniently be done when one surface of the modules defines the periphery of a wheel-like applicator unit.

In one version of the method the elastic material is first grasped by the clamping means when they are separated by a distance equivalent to the full length of the article. The clamping means are later moved closer together to define the ultimate length of the elastic unit. This movement is more simply controlled when one of the clamping means is fixed and one movable. When a plurality of modules is used, the movable clamping means of one module will be positioned next to the fixed clamping means of an adjacent module at the point where the incoming elastic is grasped. Both clamping means will grasp the elastic material essentially simultaneously, whereupon the severing means will act between them to create the elastic unit. The movable clamping means will then be positioned to the desired relationship with the fixed clamping means of its own module prior to application of the elastic unit to the article.

Apparatus for carrying out the present method is shown in the detailed description of the invention.

It is an object of this invention to provide an improved method and apparatus for applying elastic material to articles such as wearing apparel.

It is a further object to provide a method and apparatus for applying tensioned elastic to specific means of articles when such areas are of shorter linear dimension than the length of the article.

It is another object to provide a method and apparatus for applying tensioned elastic to specific areas of articles with maximum efficiency of the elastic material.

It is yet an object to provide a disposable diaper of improved appearance.

These and other objects will become evident on reference to the following detailed description and figures.

BRIEF DESCRIPTION OF THE DRAWINGS

FIG. 1 is a side elevation, partially cut away, showing the elastic applicator in position on a line manufacturing disposable diapers.

FIG. 2 is an isometric view of a typical diaper having an elastic ribbon applied near the margins of the leg areas. The diaper is shown in tension as it would be during much of the manufacturing operation.

FIG. 3 is an isometric view of the diaper shown in the previous figure with the tension relaxed.

FIG. 5 is a detailed isometric representation spanning two modules of the elastic applicator unit in which the movable clamp of one module is shown moving toward its resting position.

FIG. 6 is partial plan view of the modules shown in FIG. 5.

FIG. 7 is a detailed isometric view spanning two modules in which the movable clamp of one module is shown adjacent to the fixed clamp of the adjacent module with both clamps being in position to seize an incoming strip of elastic.

FIG. 8 is a partial plan view of the clamps shown in FIG. 7.

FIG. 9 is a fragmentary side elevation showing detail of one fixed clamp and its associated elastic severing unit.

FIG. 10 is a fragmentary isometric view of the fixed clamp in position to receive the incoming elastic ribbon.

FIG. 11 is a fragmentary transverse elevation of the representation shown in FIG. 10 taken along Section 11—11 of FIG. 9.

FIG. 12 is a fragmentary isometric view of the fixed clamp after the clamp has grasped the elastic tape, but before the tape has been severed. This figure is also taken along Section 11—11 of FIG. 9.

FIG. 13 is a transverse elevation representation of the view shown in FIG. 12.

FIG. 14 is similar to the preceeding isometric views. Here the elastic has been severed to create an individual unit of elastic.

FIG. 15 is a transverse elevation view of FIG. 14 taken along Section 11—11 of FIG. 9.

DESCRIPTION OF THE PREFERRED EMBODIMENTS

Figure 4:
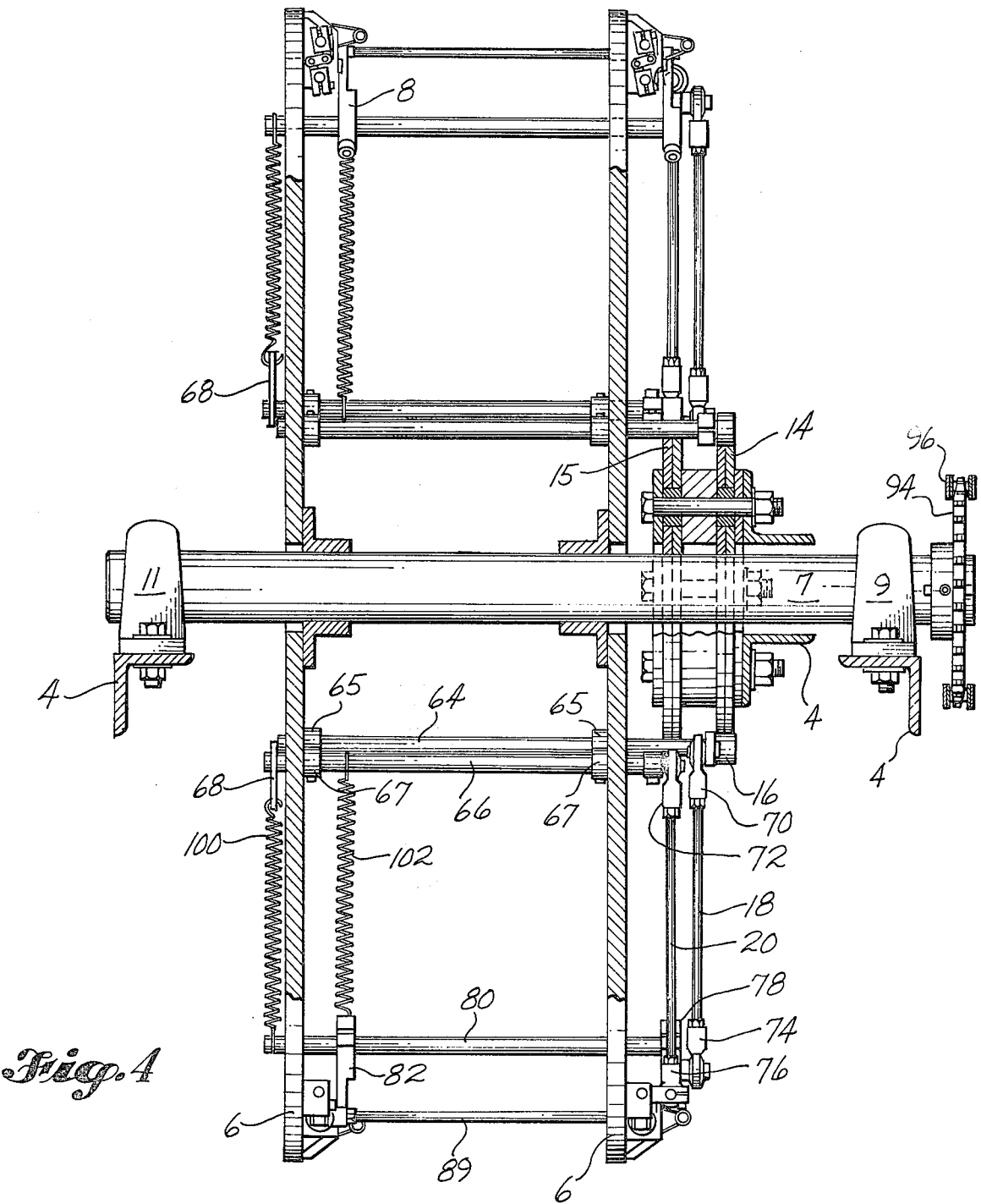
FIG. 4 is a partially cut away transverse vertical section of the elastic applicator at 90° to the representation of FIG. 1, taken through Section 1—1 of FIG. 16.

Referring now to FIG. 1, the elastic applicator is generally indicated at 2. It is shown here as part of a diaper manufacturing line, partially shown at 3. The elastic applicator is on a frame 4, here mounted on rollers 5 so that it can be readily moved in or out of the line depending on the type of diaper being manufactured. The application comprises a main rotor body 6 and a series of elastic clamping means 8 located around the periphery. The unit shown contains six elastic applicator modules. Each module consists of a movable clamp, generally shown at 10, and a fixed clamp, generally shown at 12. The clamps at 10 and 12 are not members of the same module. Clamp 12 defines the trailing end of an earlier module and clamp 10 defines the leading end of a later module. The clamps are caused to operate by cams 14 and 15. The outside cam 14 controls the position of the movable clamp. The inner cam 15 controls the opening and closing sequence of both clamps and also controls the severing of individual elastic tape units. Cam follower 16 operates through connecting rod 18 to control the position of the movable clamp. Cam follower 17 operates through connecting rod 20 to control the opening and closing sequence of the clamps and the timing of the severing means.

The elastic material, in this case shown as ribbons or tapes 23, 23, is drawn from supply 24 over friction rollers 25 which cause the tape to be tensioned as it is grasped by the clamps 8. As will be described later, the elastic is severed from the main body of tape by a severing knife to create individual elastic units 26. As the rotor body of the applicator turns, the elastic unit passes adhesive applicator 28 which applies either a continuous or intermittent line of adhesive on the elastic substance. Very typically this adhesive will be a hot melt or heat activatable type which has some flexibility at room temperature. In the illustrations shown, an impervious film 30, typically made of polyethylene, is drawn from supply roll 32 under brake roll 33 and over idler roll 34. The individual elastic units 26, now coated with adhesive, are mated to the plastic film under pressure roll 35. They are released by the clamps and carried thenceforth bonded to the plastic film, as at 36. The plastic film is normally maintained under tension when the elastic is applied in order to prevent puckering. The plastic film likewise must be maintained under adequate tensin until the individual articles, in this case diapers, are assembled and until they are severed near the end of the operation. It is within the scope of the invention to apply adhesive to the appropriate areas of the article, rather than the elastic, although this is not generally preferred.

The elastic may be applied to any appropriate article. Typically it will be a garment and in the illustrations shown the article is a disposable baby diaper. The portion of the diaper making machine represented is mounted on frame 39. This includes a roll 40 around which is passed an endless belt 42. The plastic backing film containing the individual elastic units passes around roll 40 where it is supported on the endless belt. Individual pre-cut absorbent pads 44 are laid on the plastic backing film as it passes under assembly roll 48, which imposes a very light pressure on the system. The absorbent pads are typically made from fluffed purified wood pulp. A facing material 46, typically a nonwoven fabric, is also mated to the assembly under roll 48. This nonwoven material is normally bonded to the backing film along the edges, and may also be bonded to the absorbent pads by thin streaks of hot melt adhesive applied by an applicator, which is not shown. This part of the operation is in the prior art. The thus assembled individual diapers 50 are carried on endless belt 42 to a severing station, not shown. They are maintained under sufficient tension until severed to prevent puckering of the structure in the area in which the elastic has been applied.

FIG. 2 illustrates a typical elastic-leg diaper 54 that might be constructed using the present apparatus. Diapers may optionally contain leg cutouts 58 to add to the comfort of the wearer. The diaper 54 of FIG. 2 is shown maintained under tension, as it would be during the assembly process. FIG. 3 shows the a diaper 56 after it has been severed from the assembly line, much as it would be when received by the user.

Reference is now made to FIGS. 4 through 8 to illustrate in detail the working mechanism of the elastic application unit. The movable clamp 10 is positioned by cam follower 16 riding on cam 14. The cam follower is rotatably mounted on actuating lever 60, which is fixed at its proximal end to pivot rod 64. This rod passes through the body of the rotor 6 where it is held in place by collars 65 in the interior of the rotor. Cam 15 drives cam follower 17 which, in turn, is mounted on actuating lever 62. At its proximal end this actuating lever is fixed to pivot rod 66 which passes through the body of the rotor and is retained in position by collars 67. Pivot rod 66 terminates at its end away from the cams in spring lever 68 which, in turn, is tied to spring 100. This spring severs to hold the cam follower 17 against cam 15. Actuating lever 60 severs to control the position of the movable clamps. Actuating lever 62 severs to control the opening and closing sequence of both clamps and also to operate the shear which severs the individual elastic units from the main body of elastic material. At its distal end the movable clamp positioning lever 60 is pivotally tied to an adjustable end 70 to the inner end of connecting rod 18. The outer end of this connecting rod is pivotally connected by a second adjustable end 74 to the positioning arm 78 of the movable clamp. This positioning arm is attached to pivot rod 80 which also passes through rotor body 6 to operate a similar positioning arm 82 on the other side of the unit.

The clamp/shear activation lever 62 is similarly pivotally connected as its distal end to an adjustable connecting rod end 72, located at the inner end of connecting rod 20. At its outer end, connecting rod 20 bears another adjustable end 76 which is pivotally connected to crank 84. Crank 84 is tied to the clamp/shear activating shaft 86, journaled in bearings 87, 134, which are, in turn, fixed to the frame by cap screws 88, 136.

The clamp/shear activating shaft 86 bears a second short crank 92. Crank 92 is pivotally connected to actuating rod 89 by adjustable end 90. This actuating rod also passes through the body of rotor 6 in order to operate an essentially identical mechanism on the other side of the rotor.

The rotor itself is coupled to drive shaft 7, contained in pillow block bearings 9, 11, which, in turn, are mounted to frame 4 of the elastic applicator. The shaft terminates in sprocket 94 driven through chain 96 by a drive unit, not shown.

Still referring to FIGS. 4, 5, and 7, spring 102 is connected to arm 82 in order to provide a biasing force that holds can follower 17 against cam 15. This spring also serves to hold the movable clamp 10 in the approximate position shown in FIG. 5. The normal position for this clamp would be slightly to the right of that shown in the illustration, where it would abut against the frame of rotor 6.

Movable clamp 10 will now be described in detail. It consists of a body block 112 held by cap screws 114 to the bell crank-form positioning arm 78. The clamp further comprises an anvil or fixed jaw 116 which is rigidly mounted to the body block. It additionally comprises a movable jaw 118 held by spring 120 in a position normally pressing against the anvil. Jaw 118 is attached to a short shaft 122 which passes rotatably through the body block. The other end of this shaft bears jaw actuating arm 124 which contains tang 126 (FIG. 7). This clamp is operated by two cams 128, 130 carried on clamp/shear actuating shaft 86. Cam 128 serves to open clamp 10 by bearing against tang 126 in order to release the elastic 26 at the appropriate time after it is bonded to the article. Cam 130 serves to operate clamp 10 when it is in the position shown in FIG. 7 so that incoming elastic tape may be grasped by this clamp.

Operation of the fixed clamp and elastic shearing mechanism can best be understood by referring to FIGS. 9 through 15. This clamp has a body block 134 which is attached to the rotor body 6 by cap screws 136. The clamp consists of an anvil or fixed jaw 138 along with a movable jaw 140. A third member of this unit is shear 142 which operates against the side of anvil 138 to sever individual elastic units from the main body of elastic. The shear 142 is carried on a short shaft 143 which passes rotatably through the anvil, movable jaw, and body block and is retained at its opposite end by linkage block 150. A light spring 156 serves to maintain the proper positioning of these units. The hairpin spring 144 works between movable jaw 140 and the shear 142 to maintain them normally in the relative positions shown in FIG 11. Shaft 143 passes through jaw 140 so that there is a relatively snug, yet low friction relationship. Movable jaw 140 thus pivots around shaft 143. The movable jaw 140 bears an aperture 146. Pin 148, fixed in the side of the shear element 142, extends into aperture 146 and serves as a stop against the normal action of spring 144 (FIG. 11). The shear element is moved by rotation of shaft 86 working through linkage block 152. This is tied to linkage block 150 by a pair of links 154. As shaft 86 is rotated clockwise, as seen in FIGS. 11, 13, and 15, or counterclockwise as seen in FIGS. 10, 12 and 14, clamp 140 will first close to grasp the elastic tape 126. The movement of clamp jaw 140 is actually effected indirectly through rotation of shear blade 142 by virtue of the fact that the two are flexibly connected by spring 144. As shaft 143 is rotated, movable clamp jaw 140 first drops from the positions shown in FIGS. 10 and 11 against the elastic 23 to hold it against the anvil 138, as shown in FIGS. 12 and 13. With continued rotation of shaft 143, the shear element 142 moves to the position shown in FIGS. 14 and 15 in order to sever the elastic ribbon. Overtravel of the shear element is, in part, limited by pin 148 contacting the opposite side of aperture 146.

Figure 16:
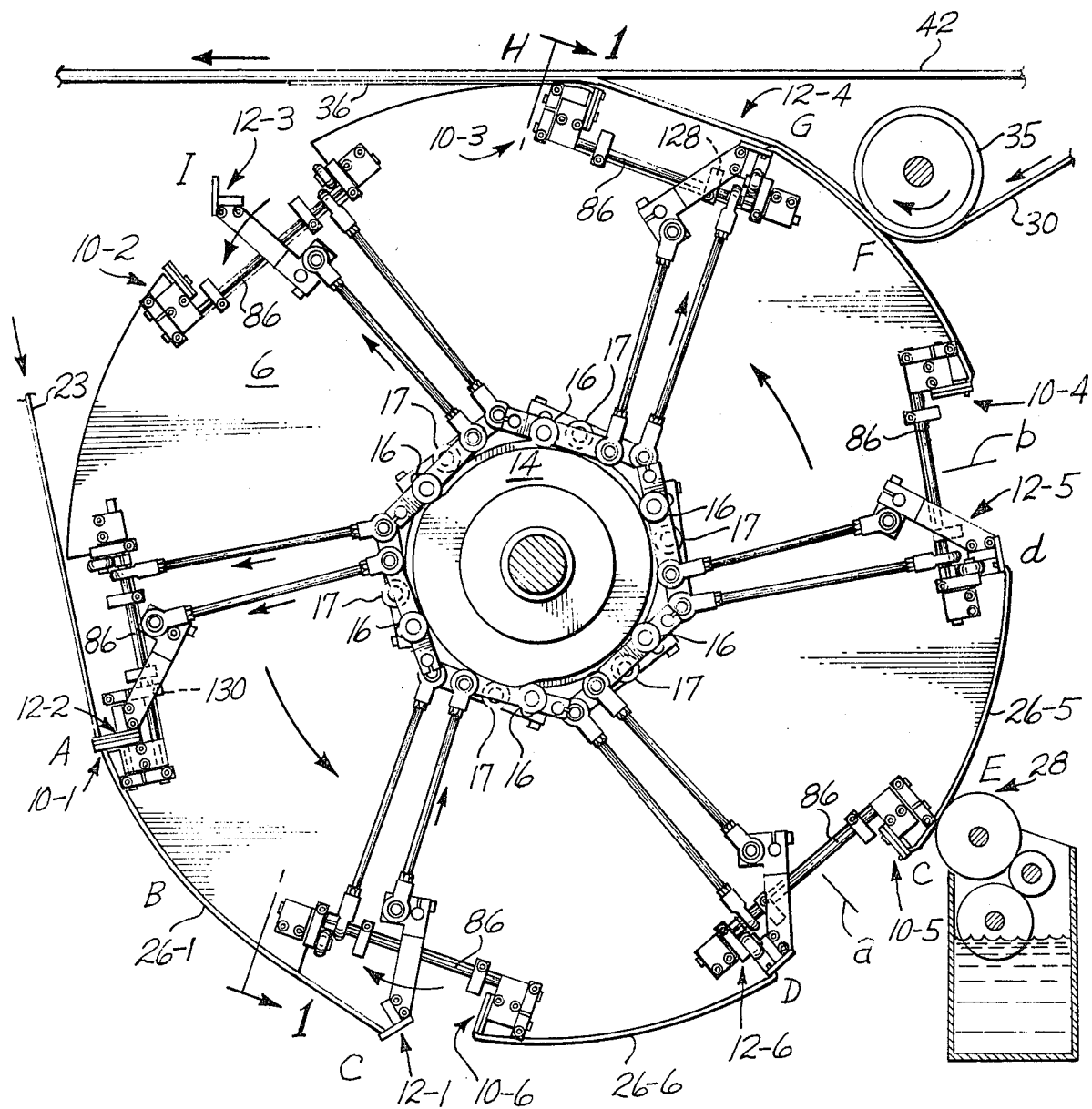
FIG. 16 is a diagrammatic side elevation view in which the total sequence of operation of the individual elastic application units can be more clearly represented.

The overall operation of the machine can now be better understood by reference to FIG. 16 with further reference to all of the preceeding figures.

The applicator represented in FIGS. 1 and 16 has six individual elastic application modules. It is convenient for one surface of each module to describe an arc equivalent to the overall length of one finished article, in this case, a diaper. In FIG. 16 a single module is illustrated on the right-hand side of the drawing between the locations a and b. These points represent the ends of a single diaper. Points c and d indicate the length of the elastic unit applied to the diaper.

The operation begins with the arrival of elastic 23, which is grasped between clamps 12-2 and 10-1 at location A. Individual modules are designated by the hyphenated number following the numbers which generally indicate the fixed clamps 10 and movable clamps 12. At location A, movable clamp 12-2 of the second module is positioned adjacent to fixed clamp 10-1 of the first module. Leading clamp 12-1 of the first module has already grasped the elastic at this time.

By the time the rotor has moved to position B, both clamps have closed to hold the elastic and the severing knife has operated between them to create an individual elastic unit 26-1. The leading end of the first elastic unit is held in clamp 12-1, while the trailing end is in clamp 10-1. Clamp 12-2 holds the leading end of the following elastic unit. By the time the rotor has advanced to position C the movable clamp, here shown as 12-1, has returned, about halfway, to its normal position. When rotor 6 has advanced to D, the movable clamp has completed its travel and is back at its resting position. In the illustration given, the movable clamp is the leading clamp of the pair. It will be obvious to one skilled in the art that the elastic applicator would be equally functional if this relationship was reversed.

At location E, the glue applicator 28 applies a film of hot melt adhesive to the surface of the elastic units 26. When the rotor has reached point F, slightly more than 180 degrees of rotation from the point at which the tapes were initially grasped, the incoming diaper backing material 30 is pressed by roll 35 against the adhesive coated tapes. By the time the rotor has traveled an additional 10 degrees or so, the leading end of the elastic will be bonded to the plastic and the movable clamp will open to release it. As the rotor continues to point H, the entire elastic unit will have been bonded to the backing and the trailing clamp will open to totally release the elastic unit from the applicator module. Shortly after this point, the movable clamp will begin its travel toward the fixed clamp of the preceding unit, as indicated at I. The two clamps will be in adjacent position by the time the rotor has again reached point A, at which time both clamps will be open in order to receive the incoming elastic and repeat the cycle.

It is evident that the rotor must be traveling in the same direction as the plastic film or other component of the article at the time the elastic unit is bonded to it. It is also desirable that they be traveling at essentially the same peripheral speed. Under some circumstances, a minor differential in speed would be permissible if it was desired to further increase or decrease the elongation of the elastic units but this would not normally be the case.

Note that at location G, it is cam 128 on shaft 86 that opens the jaws of the movable clamp to release the leading end of the elastic. At locations A and B it is can 130 on shaft 86 which serves to open and close the jaws of the movable clamp.

EXAMPLE

A six-module applicator was constructed as shown in the drawings, having a diameter of 84 cm. This was used to apply elastic to both leg openings of a medium-sized disposable baby diaper having overal dimensions 44 cm long and 32 cm wide. The backing film was a pigmented, textured polyethylene film 0.025 mm thick. The elastic was made of natural rubber and was 6.2 mm wide and 0.22 mm thick, with an extensibility in excess of 450 percent. This was bonded to the plastic backing film using an elastomeric hot melt adhesive based on a modified SBR rubber with appropriate tackifiers (Findley 995–336 made by Findley Adhesive Company, Elm Grove, Wisc.). The line speed was about 30.5 m/min, equivalent to the production of about 70 diapers per minute. The tensioned elastic units as applied were 25.5 cm in length, leaving about 9.3 cm at the end of each diaper without elastic. As bonded to the backing film, the elastic had about 180 percent stretch so that the applied unit represented about 14.2 cm of relaxed elastic. The nonfunctional material held by the clamps did not amount to more than a few millimeters at each end.

The backing film with elastic attached was combined with an hourglass-shaped fluffed wood pulp pad weighing about 35 gm. This was overlaid by nonwoven fabric weighing 20.5 g/m$^2$ and bonded to the assembly with a hotmelt adhesive. Before the individual diaper units were severed and folded, side cutouts were made as shown in FIG. 2.

Having thus described the best mode of construction and operation known, it will be apparent to one skilled in the art that many variations could be made in the apparatus and in the method of its operation without departing from the spirit of the invention. For example, it would be equally reasonable to apply the adhesive to the selected areas of the backing film. The relative positions of the fixed and movable clamps could be reversed without changing the method of operation. In the example shown, the device is applying parallel strips of elastic along opposite edges of a disposable diaper. The method and apparatus could be used to apply elastic to other articles of manufacture, such as disposable panties. Other variations will be readily apparent to those skilled in the art.

What is claimed is:

1. A method of applying units of an elastic material to a predetermined area of an article comprising:
   a. providing a continuous source of the elastic material;
   b. tensioning the elastic material;
   c. grasping the leading end of the elastic material in a first clamping means;
   d. grasping the tensioned elastic material in a second clamping means at a predetermined distance from the first clamping means, said distance being greater than the length of the elastic unit applied to the article;
   e. severing the portion of elastic held between the clamping means from the main body of elastic material at a location adjacent to the second clamping means;

f. moving the clamping means closer together to a separation which defines the length of the elastic unit applied to the article;

g. bonding the elastic unit to the desired area of at least one component of the article; and h. releasing the elastic from the clamps after the bond has been established.

2. The method of claim 1 in which the elastic unit is adhesively bonded to the component of the article.

3. The method of claim 2 in which the adhesive is applied to the elastic unit prior to contact with the component.

4. The method of claim 2 in which the adhesive is applied to the component in the area to which the elastic unit is to be bonded.

5. The method of claim 1 in which the elastic unit is bonded to the component by stitching.

6. The method of claims 1, 2, 3, 4, or 5 in which bonding preceeds from the leading end of the elastic unit and the clamping means release the elastic sequentially as bonding is effected.

7. The method of claim 1 in which the article is in a continuous sequence of moving articles.

8. The method of claim 7 in which the elastic is bonded to a component of the articles, said component being in the form of a continuous film or sheet.

9. The method of claim 8 in which the final assembly of the articles is made following bonding of the elastic units.

10. The method of claim 7 in which the length of the elastic unit is less than the length of an individual article.

11. The method of claim 10 in which at least 90 percent of the unstretched length of the elastic material is functionally bonded to the article.

12. The method of claim 11 in which the article is a disposable diaper.

13. The method of claim 1 when the first and second clamping means are in an individual elastic applicator module.

14. The method of claim 13 in which a plurality of elastic applicator modules are provided, said modules sequentially applying elastic units to an oncoming series of articles.

15. The method of claims 13 or 14 where the modules are caused to move in the same direction and at essentially the same surface speed as the articles.

16. The method of claim 14 in which the surface length of the applicator modules is equivalent to the length of the article.

17. The method of claim 16 in which:

a. the first clamping means of one module is initially located adjacent to the second clamping means of a preceeding module;

b. the incoming elastic material from the supply source is essentially simultaneously grasped by both clamping means; and c. the elastic is severed between the clamps to create the elastic unit held in the preceeding module.

* * * * *